United States Patent
Blythe (10) Patent No.: US 9,261,478 B2
(45) Date of Patent: Feb. 16, 2016

(54) SYSTEM AND METHOD FOR MEASURING AN ANALYTE IN A SAMPLE AND CALCULATING HEMATOCRIT-INSENSITIVE GLUCOSE CONCENTRATIONS

(71) Applicant: Cilag GmbH International, Zug (CH)

(72) Inventor: Stephen Patrick Blythe, Inverness (GB)

(73) Assignee: Cilag GmbH International, Zug (CH)

( * ) Notice: Subject to any disclaimer, the term of this patent is extended or adjusted under 35 U.S.C. 154(b) by 315 days.

(21) Appl. No.: 13/765,504

(22) Filed: Feb. 12, 2013

(65) Prior Publication Data

US 2014/0224674 A1    Aug. 14, 2014

(51) Int. Cl.
    *G01N 27/327* (2006.01)
(52) U.S. Cl.
    CPC .................................. *G01N 27/3274* (2013.01)
(58) Field of Classification Search
    CPC .................................. G01N 27/3271–27/3274
    See application file for complete search history.

(56) References Cited

U.S. PATENT DOCUMENTS

| | | |
|---|---|---|
| 5,762,770 A | 6/1998 | Pritchard et al. |
| 5,942,102 A | 8/1999 | Hodges et al. |
| 6,064,896 A | 5/2000 | Rosenthal |
| 6,413,410 B1 | 7/2002 | Hodges et al. |
| 7,749,371 B2 | 7/2010 | Guo et al. |
| 2011/0073494 A1 | 3/2011 | McColl et al. |
| 2013/0047415 A1 | 2/2013 | Morris et al. |

FOREIGN PATENT DOCUMENTS

| | | |
|---|---|---|
| EP | 2098857 A2 | 9/2009 |
| EP | 2416893 A1 | 2/2012 |
| WO | 2008040998 A2 | 4/2008 |
| WO | 2010099122 A1 | 9/2010 |
| WO | 2012084194 A1 | 6/2012 |

OTHER PUBLICATIONS

International Search Report and Written Opinion issued in corresponding International Application No. PCT/IB2014/058940, mailed May 26, 2014, 9 pages.

*Primary Examiner* — Alexander Noguerola (57) ABSTRACT

Described are methods and systems to apply a plurality of test voltages to the test strip and measure a current transient output resulting from an electrochemical reaction in a test chamber of the test strip so that a glucose concentration can be determined that is simpler, less error prone and provides the unexpected advantage of being insensitive to hematocrits in the blood sample.

9 Claims, 8 Drawing Sheets

SYSTEM AND METHOD FOR MEASURING AN ANALYTE IN A SAMPLE AND CALCULATING HEMATOCRIT-INSENSITIVE GLUCOSE CONCENTRATIONS

BACKGROUND

Analyte detection in physiological fluids, e.g. blood or blood derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include glucose for diabetes management, cholesterol, and the like. In response to this growing importance of analyte detection, a variety of analyte detection protocols and devices for both clinical and home use have been developed.

One type of method that is employed for analyte detection is an electrochemical method. In such methods, an aqueous liquid sample is placed into a sample-receiving chamber in an electrochemical cell that includes two electrodes, e.g., a counter and working electrode. The analyte is allowed to react with a redox reagent to form an oxidizable (or reducible) substance in an amount corresponding to the analyte concentration. The quantity of the oxidizable (or reducible) substance present is then estimated electrochemically and related to the amount of analyte present in the initial sample.

Such systems are susceptible to various modes of inefficiency or error. For example, hematocrits and interferents may affect the results of the method.

SUMMARY OF THE DISCLOSURE

Applicant has discovered a heretofore unknown and novel technique to allow for greater precision and accuracy in analyte measurements despite varying levels of substances that are present in the sample that may affect the accuracy of the analyte measurement. In one aspect, a method of determining blood glucose concentration with a glucose measurement system is provided. The system includes a test strip and test meter. The test meter has a microcontroller configured to apply a plurality of test voltages to the test strip and measure a current transient output resulting from an electrochemical reaction in a test chamber of the test strip. The method can be achieved by: initiating a test sequence after deposition of a sample; transforming glucose in the sample from one form to a different form; switching the first voltage to a second voltage different than the first voltage; changing the second voltage to a third voltage different from the second voltage; measuring a first current output of the current transient from the electrodes at least at any point during or after the switching from the first voltage to the second voltage; measuring a second current output of the current transient at least at any point during or after the third voltage is maintained in the test chamber; and calculating a blood glucose concentration based on a logarithm of a ratio of the first and second current outputs.

In yet another aspect, an analyte measurement system is provided that includes a biosensor and an analyte meter. The biosensor has at least two electrodes with reagent disposed proximate the electrodes. The analyte meter includes a port for insertion of the biosensor for electrical connection with a microcontroller of the meter and the at least two electrodes such that, upon deposition of an fluid sample, a test sequence is initiated by the microcontroller to measure first and second current outputs from voltages applied to the electrodes of the biosensor and determine an analyte concentration based on logarithm of the ratio of the first and second currents.

The following features can be combined individually with each of the above aspects or these features can be combined together with each of the above aspects for variations that are within the scope of this invention. For example, the first current output is measured at about 2.25 seconds after the start of a test sequence and the second current output is measured at about 4.4 seconds after the start of the test sequence and k may include about 2.5; the first current output may include a summation of current outputs measured from about 1 seconds after the start of the test sequence to about 4 seconds after the start of the test sequence and the second current output may include a summation of current outputs measured from about 4 seconds after the start of the test sequence to about 5 seconds after the start of the test sequence; or the calculating or calculation may include utilizing an equation of the form:

$$G = I_T + S_L * \log\left(k\left|\frac{I_1}{I_2}\right|\right) I_2$$

where G is representative of glucose concentration $I_T$ comprises an intercept resulting from linear regression analysis of a batch of test strips;

$S_L$ comprises a slope resulting from linear regression analysis of a batch of test strips;

$I_1$ comprises a first current output measured from the current transient at any time point from about 1 seconds to about 4 seconds from a start of the test sequence;

$I_2$ comprises a second current output measured from the current transient at any time point from about 4 seconds to about 5 seconds from the start of the test sequence; and k comprises a coefficient from about 1 to about 2.

In the aforementioned aspects of the disclosure, the steps recited in the methods, such as, for example, determining, estimating, calculating, computing, deriving and/or utilizing (possibly in conjunction with an equation) may be performed be an electronic circuit or a processor. These steps may also be implemented as executable instructions stored on a computer readable medium; the instructions, when executed by a computer may perform the steps of any one of the aforementioned methods.

In additional aspects of the disclosure, there are computer readable media, each medium comprising executable instructions, which, when executed by a computer, perform the steps of any one of the aforementioned methods.

In additional aspects of the disclosure, there are devices, such as test meters or analyte testing devices, each device or meter comprising an electronic circuit or processor configured to perform the steps of any one of the aforementioned methods.

These and other embodiments, features and advantages will become apparent to those skilled in the art when taken with reference to the following more detailed description of various exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

MODES FOR CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment. As used herein, "oscillating signal" includes voltage signal(s) or current signal(s) that, respectively, change polarity or alternate direction of current or are multi-directional. Also used herein, the phrase "electrical signal" or "signal" is intended to include direct current signal, alternating signal or any signal within the electromagnetic spectrum. The terms "processor"; "microprocessor"; or "microcontroller" are intended to have the same meaning and are intended to be used interchangeably. As used herein, the term "annunciated" and variations on its root term indicate that an announcement may be provided via text, audio, visual or a combination of all modes or mediums of communication to a user.

Figure 1A:
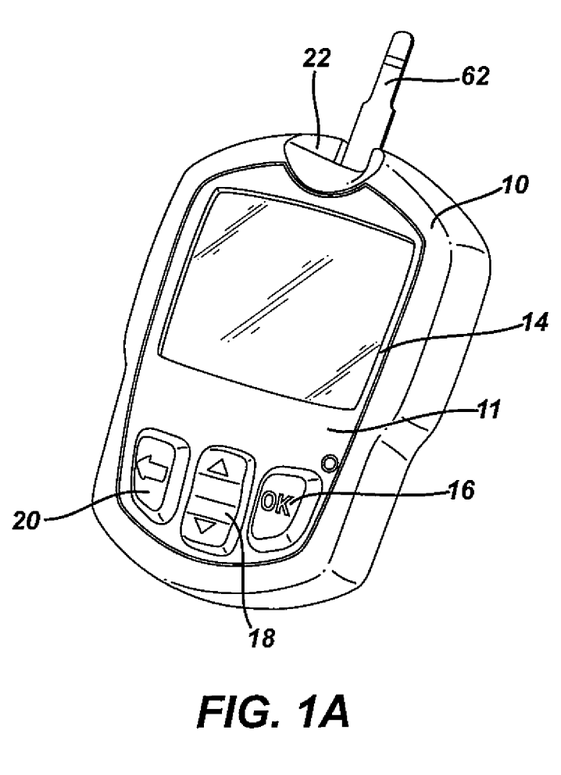
FIG. 1A illustrates a preferred blood glucose measurement system.

FIG. 1A illustrates a diabetes management system that includes a meter 10 and a biosensor in the form of a glucose test strip 62. Note that the meter (meter unit) may be referred to as an analyte measurement and management unit, a glucose meter, a meter, and an analyte measurement device. In an embodiment, the meter unit may be combined with an insulin delivery device, an additional analyte testing device, and a drug delivery device. The meter unit may be connected to a remote computer or remote server via a cable or a suitable wireless technology such as, for example, GSM, CDMA, BlueTooth, WiFi and the like.

Referring back to FIG. 1A, glucose meter or meter unit 10 may include a housing 11, user interface buttons (16, 18, and 20), a display 14, and a strip port opening 22. User interface buttons (16, 18, and 20) may be configured to allow the entry of data, navigation of menus, and execution of commands. User interface button 18 may be in the form of a two way toggle switch. Data may include values representative of analyte concentration, or information, which are related to the everyday lifestyle of an individual. Information, which is related to the everyday lifestyle, may include food intake, medication use, occurrence of health check-ups, and general health condition and exercise levels of an individual. The electronic components of meter 10 may be disposed on a circuit board 34 that is within housing 11.

Figure 1B:
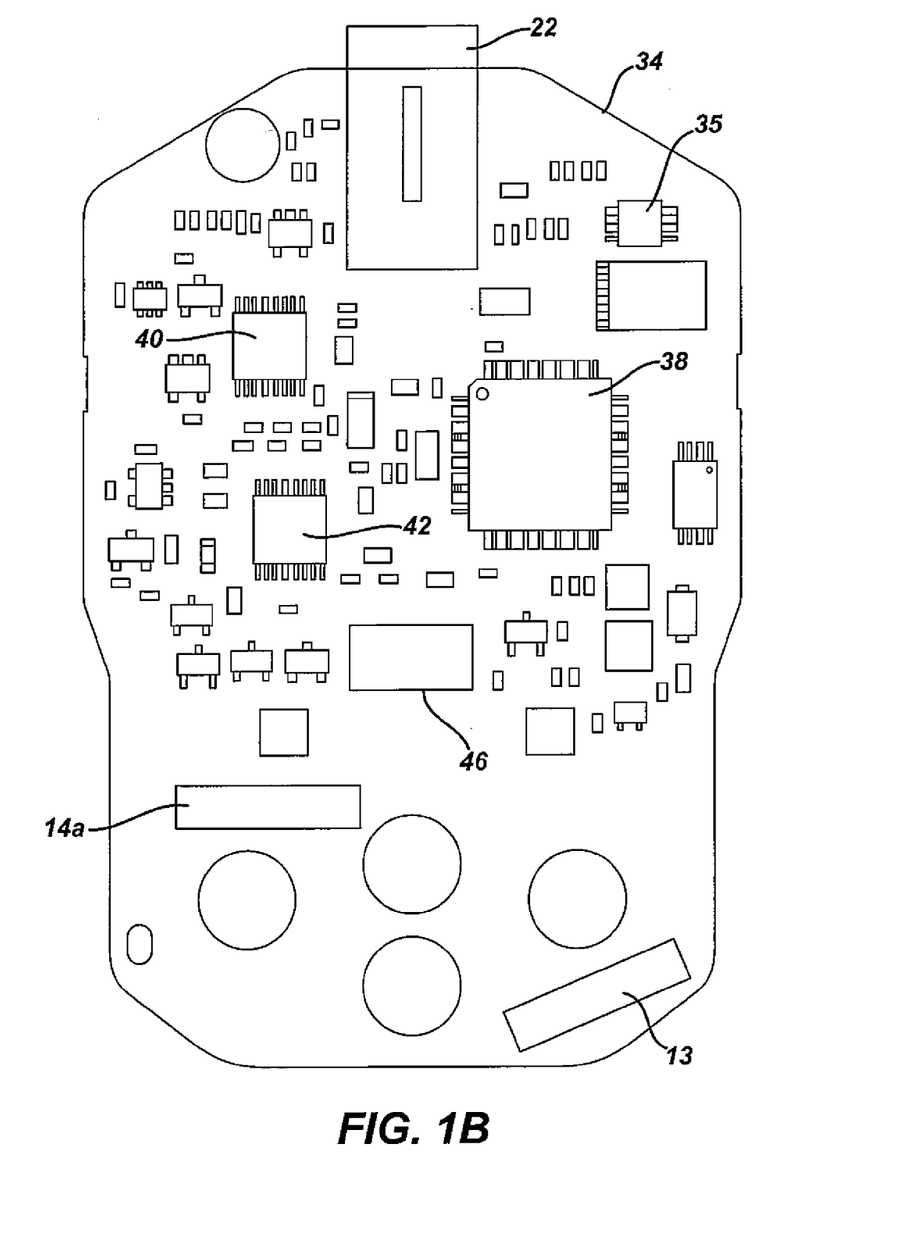
FIG. 1B illustrates the various components disposed in the meter of FIG. 1A.

FIG. 1B illustrates (in simplified schematic form) the electronic components disposed on a top surface of circuit board 34. On the top surface, the electronic components include a strip port connector 22, an operational amplifier circuit 35, a microcontroller 38, a display connector 14a, a non-volatile memory 40, a clock 42, and a first wireless module 46. On the bottom surface, the electronic components may include a battery connector (not shown) and a data port 13. Microcontroller 38 may be electrically connected to strip port connector 22, operational amplifier circuit 35, first wireless module 46, display 14, non-volatile memory 40, clock 42, battery, data port 13, and user interface buttons (16, 18, and 20).

Operational amplifier circuit 35 may include two or more operational amplifiers configured to provide a portion of the potentiostat function and the current measurement function. The potentiostat function may refer to the application of a test voltage between at least two electrodes of a test strip. The current function may refer to the measurement of a test current resulting from the applied test voltage. The current measurement may be performed with a current-to-voltage converter. Microcontroller 38 may be in the form of a mixed signal microprocessor (MSP) such as, for example, the Texas Instrument MSP 430. The TI-MSP 430 may be configured to also perform a portion of the potentiostat function and the current measurement function. In addition, the MSP 430 may also include volatile and non-volatile memory. In another embodiment, many of the electronic components may be integrated with the microcontroller in the form of an application specific integrated circuit (ASIC).

Strip port connector 22 may be configured to form an electrical connection to the test strip. Display connector 14a may be configured to attach to display 14. Display 14 may be in the form of a liquid crystal display for reporting measured glucose levels, and for facilitating entry of lifestyle related information. Display 14 may optionally include a backlight. Data port 13 may accept a suitable connector attached to a connecting lead, thereby allowing glucose meter 10 to be linked to an external device such as a personal computer. Data port 13 may be any port that allows for transmission of data such as, for example, a serial, USB, or a parallel port. Clock 42 may be configured to keep current time related to the geographic region in which the user is located and also for measuring time. The meter unit may be configured to be electrically connected to a power supply such as, for example, a battery.

Figures 1C, 1D:
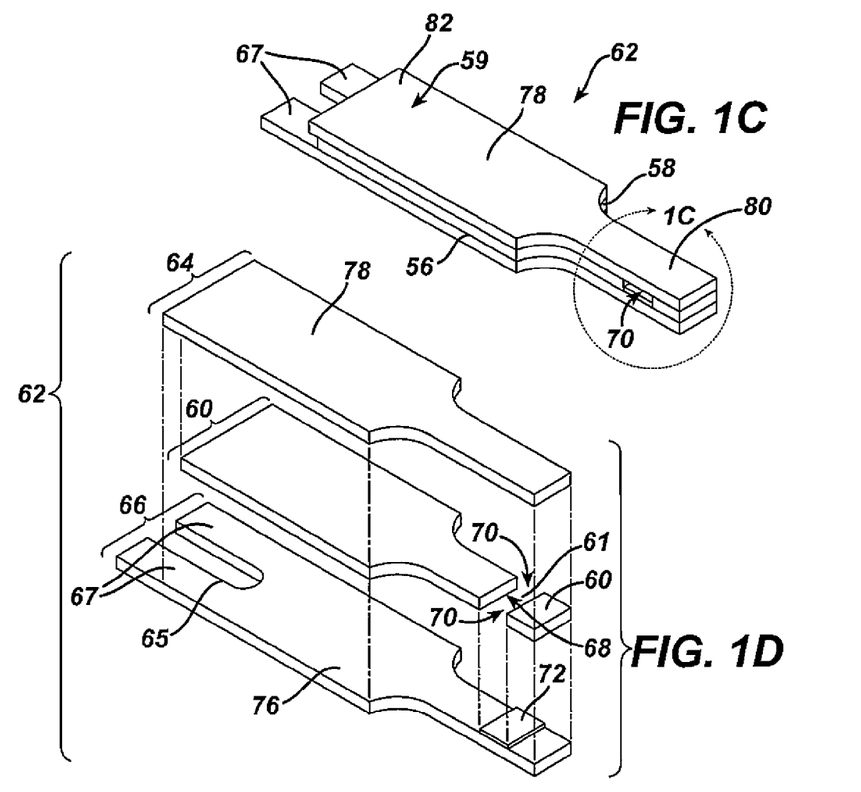
FIG. 1C illustrates a perspective view of an assembled test strip suitable for use in the system and methods disclosed herein.
FIG. 1D illustrates an exploded perspective view of an unassembled test strip suitable for use in the system and methods disclosed herein.
Figure 1E:
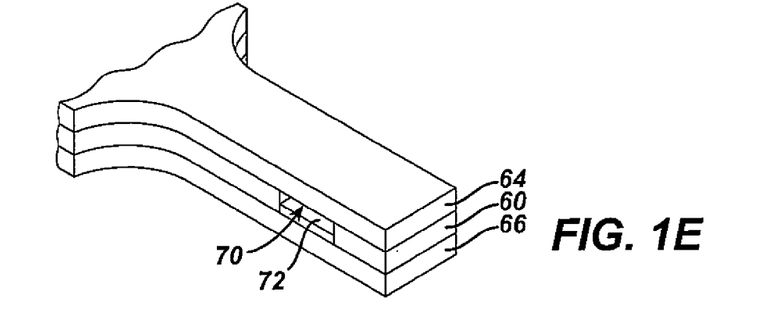
FIG. 1E illustrates an expanded perspective view of a proximal portion of the test strip suitable for use in the system and methods disclosed herein.
Figures 2, 3:
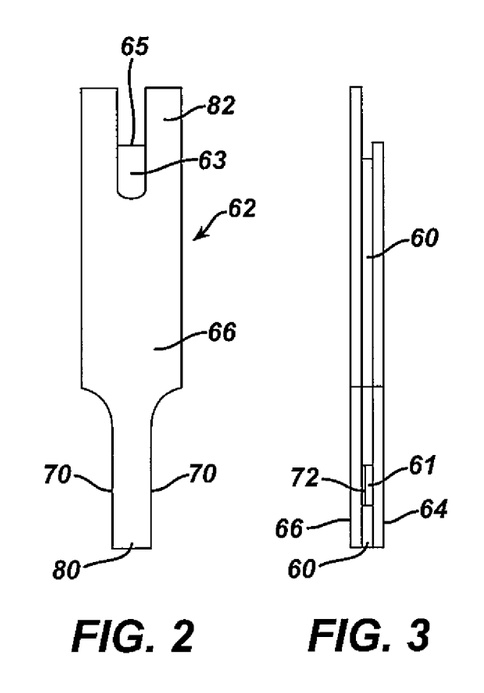
FIG. 2 is a bottom plan view of one embodiment of a test strip disclosed herein.
FIG. 3 is a side plan view of the test strip of FIG. 2.
Figure 4A:
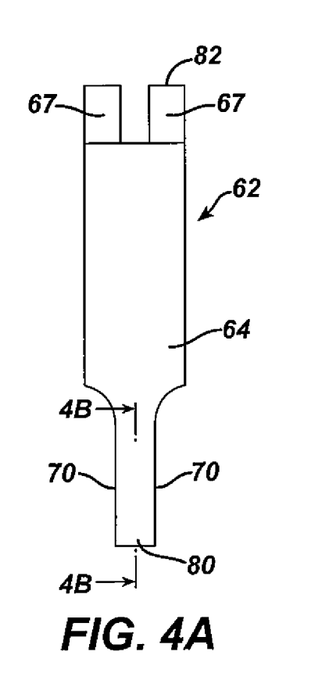
FIG. 4A is a top plan view of the test strip of FIG. 3.
Figure 4B:
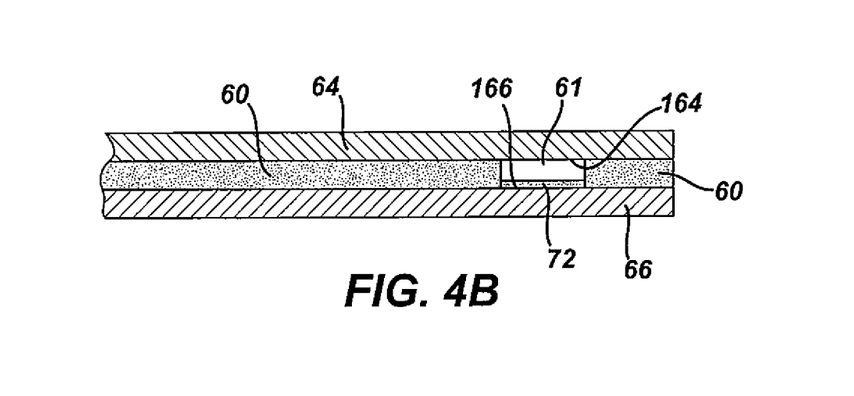
FIG. 4B is a partial side view of a proximal portion of the test strip of FIG. 4A.

FIGS. 1C-1E, 2, 3, and 4B show various views of an exemplary test strip 62 suitable for use with the methods and systems described herein. In an exemplary embodiment, a test strip 62 is provided which includes an elongate body extending from a distal end 80 to a proximal end 82, and having lateral edges 56, 58, as illustrated in FIG. 1C. As shown in FIG. 1D, the test strip 62 also includes a first electrode layer 66, a second electrode layer 64, and a spacer 60 sandwiched in between the two electrode layers 64 and 66. The first electrode layer 66 may include a first electrode 66, a first connection track 76, and a first contact pad 67, where the first connection track 76 electrically connects the first electrode 66 to the first contact pad 67, as shown in FIGS. 1D and 4B. Note that the first electrode 66 is a portion of the first electrode layer 66 that is immediately underneath the reagent layer 72, as indicated by FIGS. 1D and 4B. Similarly, the second electrode layer 64 may include a second electrode 64, a second connection track 78, and a second contact pad 63, where the second connection track 78 electrically connects the second electrode 64 with the second contact pad 63, as shown in FIGS. 1D, 2, and 4B. Note that the second electrode 64 is a portion of the second electrode layer 64 that is above the reagent layer 72, as indicated by FIG. 4B.

As shown, the sample-receiving chamber 61 is defined by the first electrode 66, the second electrode 64, and the spacer 60 near the distal end 80 of the test strip 62, as shown in FIGS. 1D and 4B. The first electrode 66 and the second electrode 64 may define the bottom and the top of sample-receiving chamber 61, respectively, as illustrated in FIG. 4B. A cutout area 68 of the spacer 60 may define the sidewalls of the sample-receiving chamber 61, as illustrated in FIG. 4B. In one aspect, the sample-receiving chamber 61 may include ports 70 that provide a sample inlet or a vent, as shown in FIGS. 1C to 1E. For example, one of the ports may allow a fluid sample to ingress and the other port may allow air to egress.

In an exemplary embodiment, the sample-receiving chamber 61 (or test cell or test chamber) may have a small volume. For example, the chamber 61 may have a volume in the range of from about 0.1 microliters to about 5 microliters, about 0.2 microliters to about 3 microliters, or, preferably, about 0.3 microliters to about 1 microliter. To provide the small sample volume, the cutout 68 may have an area ranging from about 0.01 $cm^2$ to about 0.2 $cm^2$, about 0.02 $cm^2$ to about 0.15 $cm^2$, or, preferably, about 0.03 $cm^2$ to about 0.08 $cm^2$. In addition, first electrode 66 and second electrode 64 may be spaced apart in the range of about 1 micron to about 500 microns, preferably between about 10 microns and about 400 microns, and more preferably between about 40 microns and about 200 microns. The relatively close spacing of the electrodes may also allow redox cycling to occur, where oxidized mediator generated at first electrode 66, may diffuse to second electrode 64 to become reduced, and subsequently diffuse back to first electrode 66 to become oxidized again. Those skilled in the art will appreciate that various such volumes, areas, or spacing of electrodes is within the spirit and scope of the present disclosure.

In one embodiment, the first electrode layer 66 and the second electrode layer 64 may be a conductive material formed from materials such as gold, palladium, carbon, silver, platinum, tin oxide, iridium, indium, or combinations thereof (e.g., indium doped tin oxide). In addition, the electrodes may be formed by disposing a conductive material onto an insulating sheet (not shown) by a sputtering, electroless plating, or a screen-printing process. In one exemplary embodiment, the first electrode layer 66 and the second electrode layer 64 may be made from sputtered palladium and sputtered gold, respectively. Suitable materials that may be employed as spacer 60 include a variety of insulating materials, such as, for example, plastics (e.g., PET, PETG, polyimide, polycarbonate, polystyrene), silicon, ceramic, glass, adhesives, and combinations thereof. In one embodiment, the spacer 60 may be in the form of a double sided adhesive coated on opposing sides of a polyester sheet where the adhesive may be pressure sensitive or heat activated. Applicants note that various other materials for the first electrode layer 66, the second electrode layer 64, or the spacer 60 are within the spirit and scope of the present disclosure.

Either the first electrode 66 or the second electrode 64 may perform the function of a working electrode depending on the magnitude or polarity of the applied test voltage. The working electrode may measure a limiting test current that is proportional to the reduced mediator concentration. For example, if the current limiting species is a reduced mediator (e.g., ferrocyanide), then it may be oxidized at the first electrode 66 as long as the test voltage is sufficiently greater than the redox mediator potential with respect to the second electrode 64. In such a situation, the first electrode 66 performs the function of the working electrode and the second electrode 64 performs the function of a counter/reference electrode. Applicants note that one may refer to a counter/reference electrode simply as a reference electrode or a counter electrode. A limiting oxidation occurs when all reduced mediator has been depleted at the working electrode surface such that the measured oxidation current is proportional to the flux of reduced mediator diffusing from the bulk solution towards the working electrode surface. The term "bulk solution" refers to a portion of the solution sufficiently far away from the working electrode where the reduced mediator is not located within a depletion zone. It should be noted that unless otherwise stated for test strip 62, all potentials applied by test meter 10 will hereinafter be stated with respect to second electrode 64.

Similarly, if the test voltage is sufficiently less than the redox mediator potential, then the reduced mediator may be oxidized at the second electrode 64 as a limiting current. In such a situation, the second electrode 64 performs the function of the working electrode and the first electrode 66 performs the function of the counter/reference electrode.

Initially, an analysis may include introducing a quantity of a fluid sample into a sample-receiving chamber 61 via a port 70. In one aspect, the port 70 or the sample-receiving chamber 61 may be configured such that capillary action causes the fluid sample to fill the sample-receiving chamber 61. The first electrode 66 or second electrode 64 may be coated with a hydrophilic reagent to promote the capillarity of the sample-receiving chamber 61. For example, thiol derivatized reagents having a hydrophilic moiety such as 2-mercaptoethane sulfonic acid may be coated onto the first electrode or the second electrode.

In the analysis of strip 62 above, reagent layer 72 can include glucose dehydrogenase (GDH) based on the PQQ co-factor and ferricyanide. In another embodiment, the enzyme GDH based on the PQQ co-factor may be replaced with the enzyme GDH based on the FAD co-factor. When blood or control solution is dosed into a sample reaction chamber 61, glucose is oxidized by $GDH_{(ox)}$ and in the process converts $GDH_{(ox)}$ to $GDH_{(red)}$, as shown in the chemical transformation T.1 below. Note that $GDH_{(ox)}$ refers to the oxidized state of GDH, and $GDH_{(red)}$ refers to the reduced state of GDH.

D-Glucose+$GDH_{(ox)}$→Gluconic acid+$GDH_{(red)}$  T.1

Next, $GDH_{(red)}$ is regenerated back to its active oxidized state by ferricyanide (i.e. oxidized mediator or $Fe(CN)_6^{3-}$) as shown in chemical transformation T.2 below. In the process of regenerating $GDH_{(ox)}$, ferrocyanide (i.e. reduced mediator or $Fe(CN)_6^{4-}$) is generated from the reaction as shown in T.2:

$GDH_{(red)}$+2 $Fe(CN)_6^{3-}$→$GDH_{(ox)}$+2 $Fe(CN)_6^{4-}$  T.2

Figure 5:
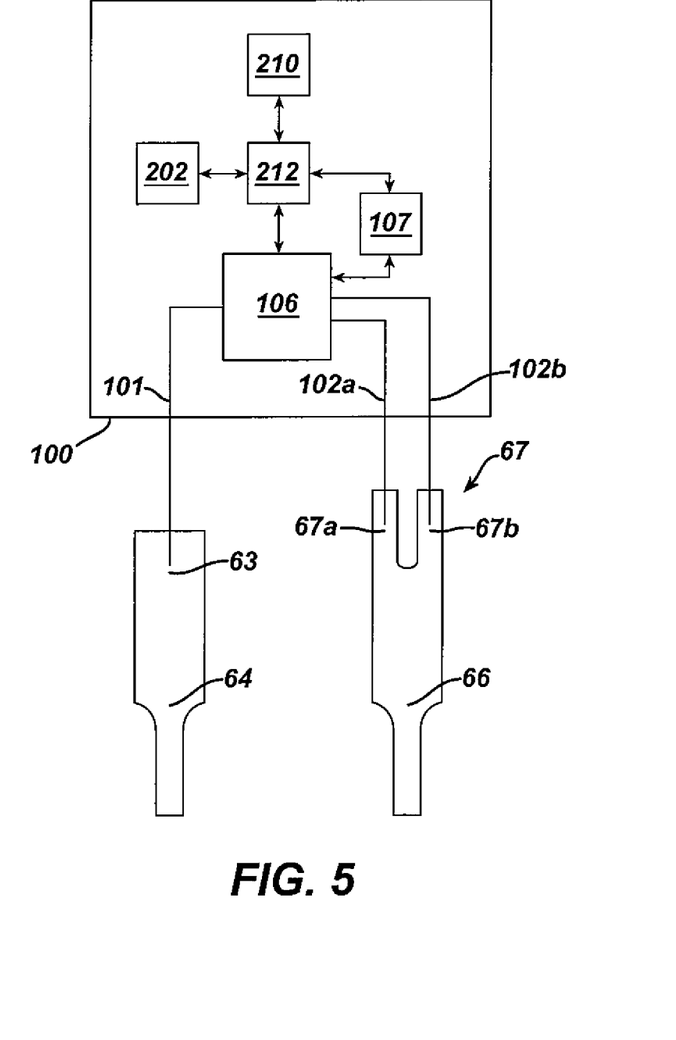
FIG. 5 is a simplified schematic showing a test meter electrically interfacing with portions of a test strip disclosed herein.

FIG. 5 provides a simplified schematic showing a test meter 100 interfacing with a first contact pad 67a, 67b and a second contact pad 63. The second contact pad 63 may be used to establish an electrical connection to the test meter through a U-shaped notch 65, as illustrated in FIG. 2. In one embodiment, the test meter 100 may include a second electrode connector 101, and a first electrode connectors (102a, 102b), a test voltage unit 106, a current measurement unit 107, a processor 212, a memory unit 210, and a visual display 202, as shown in FIG. 5. The first contact pad 67 may include two prongs denoted as 67a and 67b. In one exemplary embodiment, the first electrode connectors 102a and 102b separately connect to prongs 67a and 67b, respectively. The second electrode connector 101 may connect to second contact pad 63. The test meter 100 may measure the resistance or electrical continuity between the prongs 67a and 67b to determine whether the test strip 62 is electrically connected to the test meter 10. The electrodes 64 and 66 here can be utilized to detect physical characteristics of the sample using alternating signals. Alternatively, separate additional electrodes can be provided in the test chamber to allow for detection of the physical characteristics of the sample using alternating signals.

Figure 6A:
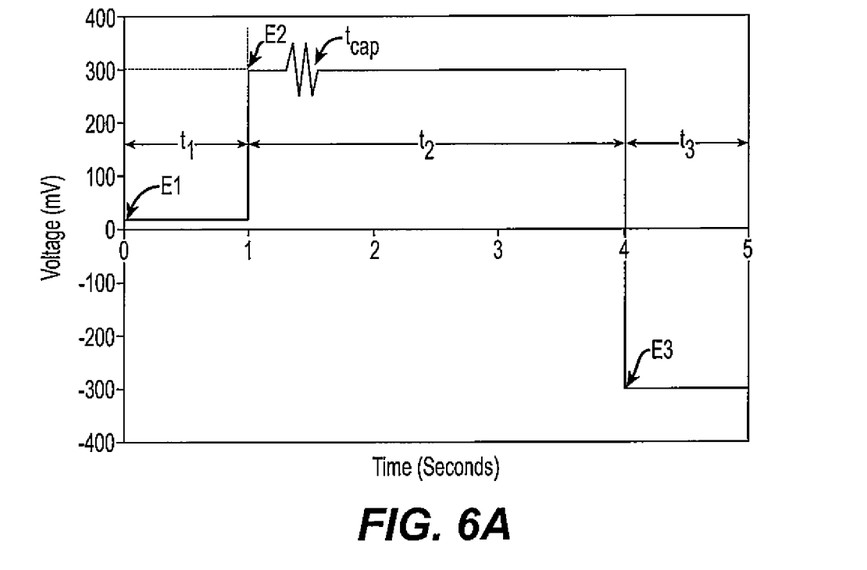
FIG. 6A shows an example of a tri-pulse potential waveform applied by the test meter of FIG. 5 to the working and counter electrodes for prescribed time intervals.

FIG. 6A is an exemplary chart of a plurality of test voltages applied to the test strip 62 for prescribed intervals. The plurality of test voltages may include a first test voltage E1 for a first time interval $t_1$, a second test voltage E2 for a second time interval $t_2$, and a third test voltage E3 for a third time interval $t_3$. The third voltage E3 may be different in the magnitude of the electromotive force, in polarity, or combinations of both with respect to the second test voltage E2. In the preferred embodiments, E3 may be of the same magnitude as E2 but opposite in polarity. A glucose test time interval $t_G$ represents an amount of time to perform the glucose test (but not necessarily all the calculations associated with the glucose test). Glucose test time interval $t_G$ may range from about 1.1 seconds to about 5 seconds. Further, as illustrated in FIG. 6A, the second test voltage E2 may include a direct (DC) test voltage component and a superimposed alternating (AC), or alternatively oscillating, test voltage component. The superimposed alternating or oscillating test voltage component may be applied for a time interval indicated by $t_{cap}$.

The plurality of test current values measured during any of the time intervals may be performed at a sampling frequency ranging from about 1 measurement per microsecond to about one measurement per 100 milliseconds and preferably at about every 50 milliseconds. While an embodiment using three test voltages in a serial manner is described, the glucose test may include different numbers of open-circuit and test voltages. For example, as an alternative embodiment, the glucose test could include an open-circuit for a first time interval, a second test voltage for a second time interval, and a third test voltage for a third time interval. It should be noted that the reference to "first," "second," and "third" are chosen for convenience and do not necessarily reflect the order in which the test voltages are applied. For instance, an embodiment may have a potential waveform where the third test voltage may be applied before the application of the first and second test voltage.

In this exemplary system, the process for the system may apply a first test voltage E1 (e.g., approximately 20 mV in FIG. 6A) between first electrode 66 and second electrode 64 for a first time interval $t_1$ (e.g., 1 second in FIG. 6A). The first time interval $t_1$ may range from about 0.1 seconds to about 3 seconds and preferably range from about 0.2 seconds to about 2 seconds, and most preferably range from about 0.3 seconds to about 1.1 seconds.

Figure 6B:
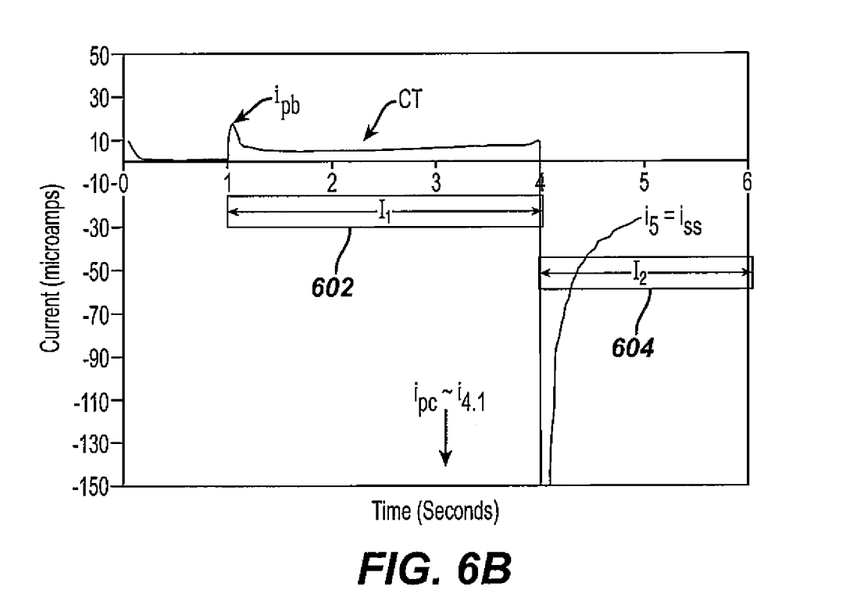
FIG. 6B shows a current transient CT generated by a physiological sample due to application of the voltages applied in FIG. 6A.

The first time interval $t_1$ may be sufficiently long so that the sample-receiving or test chamber 61 (defined partly by first wall 164 and second wall 166) may fully fill with sample and also so that the reagent layer 72 may at least partially dissolve or solvate. In one aspect, the first test voltage E1 may be a value relatively close to the redox potential of the mediator so that a relatively small amount of a reduction or oxidation current is measured. FIG. 6B shows that a relatively small amount of current is observed during the first time interval $t_1$ compared to the second and third time intervals $t_2$ and $t_3$. For example, when using ferricyanide or ferrocyanide as the mediator, the first test voltage E1 in FIG. 6A may range from about 1 millivolts ("mV") to about 100 mV, preferably range from about 5 mV to about 50 mV, and most preferably range from about 10 mV to about 30 mV. Although the applied voltages are given as positive values in the preferred embodiments, the same voltages in the negative domain could also be utilized to accomplish the intended purpose of the claimed invention.

Referring back to FIG. 6A, after applying the first test voltage E1, the test meter 10 (via the microcontroller) applies a second test voltage E2 between first electrode 66 and second electrode 64 (e.g., approximately 300 mVolts in FIG. 6A), for a second time interval $t_2$ (e.g., about 3 seconds in FIG. 6A). The second test voltage E2 may be a value different than the first test voltage E1 and may be sufficiently negative of the mediator redox potential so that a limiting oxidation current is measured at the second electrode 64. For example, when using ferricyanide or ferrocyanide as the mediator, the second test voltage E2 may range from about zero mV to about 600 mV, preferably range from about 100 mV to about 600 mV, and more preferably is about 300 mV.

The second time interval $t_2$ should be sufficiently long so that the rate of generation of reduced mediator (e.g., ferrocyanide) may be monitored based on the magnitude of a limiting oxidation current. Reduced mediator is generated by enzymatic reactions with the reagent layer 72. During the second time interval $t_2$, a limiting amount of reduced mediator is oxidized at second electrode 64 and a non-limiting amount of oxidized mediator is reduced at first electrode 66 to form a concentration gradient between first electrode 66 and second electrode 64.

In an exemplary embodiment, the second time interval $t_2$ should also be sufficiently long so that a sufficient amount of ferricyanide may be diffused to the second electrode 64 or diffused from the reagent on the first electrode. A sufficient amount of ferricyanide is required at the second electrode 64 so that a limiting current may be measured for oxidizing ferrocyanide at the first electrode 66 during the third test voltage E3. The second time interval $t_2$ may be less than about 60 seconds, and preferably may range from about 1.1 seconds to about 10 seconds, and more preferably range from about 2 seconds to about 5 seconds. Likewise, the time interval indicated as $t_{cap}$ in FIG. 6A may also last over a range of times, but in one exemplary embodiment it has a duration of about 20 milliseconds. In one exemplary embodiment, the superimposed alternating test voltage component is applied after about 0.3 seconds to about 0.4 seconds after the application of the second test voltage E2, and induces a sine wave having a frequency of about 109 Hz with an amplitude of about +/−50 mV.

FIG. 6B shows a relatively small peak $i_{pb}$ after the beginning of the second time interval $t_2$ followed by a gradual increase of an absolute value of an oxidation current during the second time interval $t_2$. The small peak $i_{pb}$ occurs due oxidation of endogenous or exogenous reducing agents (e.g., uric acid) after a transition from first voltage E1 to second voltage E2. Thereafter, there is a gradual absolute decrease in oxidation current after the small peak $i_{pb}$ is caused by the generation of ferrocyanide by reagent layer 72, which then diffuses to second electrode 64.

After application of the second test voltage E2, the test meter 10 applies a third test voltage E3 between the first electrode 66 and the second electrode 64 (e.g., about −300 mVolts in FIG. 6A) for a third time interval $t_3$ (e.g., 1 second in FIG. 6A). The third test voltage E3 may be a value sufficiently positive of the mediator redox potential so that a limiting oxidation current is measured at the first electrode 66. For example, when using ferricyanide or ferrocyanide as the mediator, the third test voltage E3 may range from about zero mV to about −600 mV, preferably range from about −100 mV to about −600 mV, and more preferably is about −300 mV.

The third time interval $t_3$ may be sufficiently long to monitor the diffusion of reduced mediator (e.g., ferrocyanide) near the first electrode 66 based on the magnitude of the oxidation current. During the third time interval $t_3$, a limiting amount of reduced mediator is oxidized at first electrode 66 and a non-limiting amount of oxidized mediator is reduced at the second electrode 64. The third time interval $t_3$ may range from about 0.1 seconds to about 5 seconds and preferably range from about 0.3 seconds to about 3 seconds, and more preferably range from about 0.5 seconds to about 2 seconds.

FIG. 6B shows a relatively large peak $i_{pc}$ at the beginning of the third time interval $t_3$ followed by a decrease to a steady-state current $i_{ss}$ value. In one embodiment, the second test voltage E2 may have a first polarity and the third test voltage E3 may have a second polarity that is opposite to the first polarity. In another embodiment, the second test voltage E2 may be sufficiently negative of the mediator redox potential and the third test voltage E3 may be sufficiently positive of the mediator redox potential. The third test voltage E3 may be applied immediately after the second test voltage E2. However, one skilled in the art will appreciate that the magnitude and polarity of the second and third test voltages may be chosen depending on the manner in which analyte concentration is determined.

Referring to FIG. 6B, the system also measure a second current output of the current transient from the electrodes after the changing from the second voltage to the third voltage and then the system proceeds by estimating a current that approximates a steady state current output of the current transient after the third voltage is maintained at the electrodes.

Thereafter, the system calculates a blood glucose concentration based on the first, second and third current outputs of the current transient and the analyte calculation coefficients. In particular, the glucose concentration G may be calculated using a glucose algorithm as shown in Equation 1:

$$G = \left(\frac{|i_2|}{|i_3|}\right)^p (a \times i_1 - z) \qquad \text{Eq. 1}$$

Where
$i_1$ is a first test current value,
$i_2$ is a second test current value,
$i_3$ is a third test current value, and
the terms a, p, and z can be empirically derived analyte calculation coefficients.

All test current values (e.g., $i_1$, $i_2$, and $i_3$) in Equation 1 use the absolute value of the current. The first test current value $i_1$ and the second test current value $i_2$ can each be defined by an average or summation of one or more predetermined test current values that occur during the third time interval $t_3$. The term $i_2$ is a second current value that is based on a fourth current value $i_4$, a fifth current value $i_5$, and a sixth current value $i_6$ measured during a third time interval. The third test current value $i_3$ can be defined by an average or summation of one or more predetermined test current values that occur during the second time interval $t_2$. One skilled in the art will appreciate that names "first," "second," and "third" are chosen for convenience and do not necessarily reflect the order in which the current values are calculated. A derivation of Eq. 1 can be found in U.S. Pat. No. 7,749,371, patented Jul. 6, 2010, which was filed on 30 Sep., 2005 and entitled "Method and Apparatus for Rapid Electrochemical Analysis," which is hereby incorporated by reference in its entirety into this application.

Referring now to FIGS. 6A and 6B, the peak current (FIG. 6B) observed at the end of $t_1$ and the beginning of the second test potential time interval $t_2$ (FIG. 6A) may be denoted as $i_{pb}$, and the peak current exhibited at the start of the third test potential time interval $t_3$ (FIG. 6A) may be denoted as $i_{pc}$. Equation 2 describes a relationship between the first current transient CT and second current transient CT when a test strip 62 is tested with a sample containing an interferent and no glucose.

$$i_{pc} - 2i_{pb} = -i_{ss} \qquad \text{Eq. 2}$$

In the case where there is no glucose in the sample, it is believed that the reagent layer 72 does not generate substantial amount of reduced mediator. Therefore, the current transients would reflect only the oxidation of interferents. At the early time scale regime of around 1.0 seconds, it is assumed that reagent layer 72 does not generate a significant amount of reduced mediator because of the glucose reaction. Further, it is assumed that the reduced mediator which is generated will mostly remain near first electrode 66, where reagent layer 72 was initially deposited, and not significantly diffuse to second electrode 64. Therefore, the magnitude of $i_{pb}$ is predominantly ascribed to interferent oxidation at second electrode 64 which is a direct interferent current.

At a duration after the third voltage E3 has been provided to the strip (e.g., about −300 mV) at around 4.1 seconds, reagent layer 72 does generate a significant amount of reduced mediator at first electrode 66 in the presence of glucose because of the glucose reaction. A significant amount of reduced mediator can also be generated because of a possible oxidation of an interferent with the oxidized mediator. As mentioned earlier, interferent that reduces oxidized mediator contributes to a current which may be referred to as an indirect current. In addition, interferents can also be oxidized directly at first electrode 66 which may be referred to as a direct current. For the situation in which the mediator can be oxidized at the working electrode, it may be assumed that the sum of the direct oxidation and indirect oxidation is approximately equal to a direct oxidation current that would have been measured if there was no oxidized mediator disposed on the working electrode. In summary, the magnitude of the $i_{pc}$ is ascribed to both indirect and direct interferent oxidation, and the glucose reaction at the first electrode 66. Because it has been determined that $i_{pb}$ is controlled mainly by interferents, $i_{pc}$ can be used with $i_{pb}$ together to determine a correction factor. For example, as shown below $i_{pb}$ can be used with $i_{pc}$ in a mathematical function to determine a corrected current $i_{2(Corr)}$ which is proportional to glucose and less sensitive to interferents:

$$i_{2(CORR)} = i_2 \left[ \frac{|i_{pc}| - |2i_{pb}| + |i_{ss}|}{|i_{pc}| + |i_{ss}|} \right] \quad \text{Eq. 3}$$

It is noted that $i_{pb}$ is measured after the start of the second test potential time interval $t_2$ and $i_{pc}$ is measured at the start of the third test potential time interval $t_3$. Applicants note that $i_{pc}$ may be the test current value at about 4.1 seconds, and $i_{pb}$ may be the test current value at about 1.1 second, based on the test voltage and test current waveforms in FIGS. 6A and 6B.

Eq. 3 was empirically derived to calculate a current $i_{2\,(Corr)}$ which is proportional to glucose and has a relative fraction of current removed that is ascribed to interferents. The term $i_{ss}$ was added to both the numerator and denominator to allow the numerator to approach zero when no glucose is present. Determination of the steady-state current $i_{ss}$ following application of the second electric potential is detailed in U.S. Pat. No. 8,163,162, which is incorporated by reference into this application herein. Other examples of methods for calculating $i_{ss}$ can be found in U.S. Pat. Nos. 5,942,102 and 6,413,410, each of which is hereby incorporated by reference in its entirety.

Next, $i_{ss}$ is estimated by multiplying the test current value at about 5 seconds with a constant $K_8$ (e.g., 0.678). Thus, $i_{ss}$ can be approximated as $i\,(5) \times K_8$. The term $K_8$ can be estimated using Equation 4 where the number 0.975 is about the time in seconds after the third test voltage E3 is applied that corresponds to the current at approximately 5 seconds for the particular embodiment of the strip 62, which, assuming a linear variation over the time between about 0.95 seconds and 1 second, is the average current between 0.95 and 1 second, the term D is assumed to be about $5 \times 10^{-6}\,\text{cm}^2/\text{sec}$ as a typical diffusion coefficient in blood, and the term L is assumed to be about 0.0095 cm, which represents the height of the spacer 60:

$$iss = \frac{i(5)}{1 + 4\exp\left(\frac{-4\pi^2 D x 0.975}{L^2}\right)} \quad \text{Eq. 4}$$

Hence, a first blood glucose concentration G can be determined by Equation 5 that utilizes current $i_{2\,(Corr)}$, (which is proportional to glucose and has a relative fraction of current removed that is ascribed to interferents):

$$G = \left(\frac{|i_r|}{|i_l|}\right)^p (a|i_{2CORR}| - zgr); \quad \text{Eq. 5}$$

where:

$$i_r = \sum_{t=4.4}^{t=5} i(t);$$

$$i_l = \sum_{t=1.4}^{t=4} i(t);$$

$$i_{2(Corr)} = i_{2(Corr)} = \left(\frac{|i_{pc}| + b|i_{ss}| - c|i_{pb}|}{|i_{pc}| + b|i_{ss}|}\right) i_r; \quad \text{Eq. 5.1}$$

and

Where a, b, c, p, and zgr are glucose calculation coefficients.

Although the applied voltages are given as positive values in the preferred embodiments, the same voltages in the negative domain could also be utilized to accomplish the intended purpose of the claimed invention.

In this exemplary embodiment, $i_{pb}$ is the current measured at approximately 1.1 second; $i_{pc}$ is current measured from the electrodes of the strip 62 at approximately 4.1 seconds; $i_{ss}$ is the current measured at approximately 5 seconds. For ease of notation, Eq. 5.1 for this known glucose concentration calculation, can be represented in the following notation as Equation 5.2:

$$i_{2(Corr)} = \left(\frac{|i_{4.1}| + b|i_5| - c|i_{1.1}|}{|i_{4.1}| + b|i_5|}\right) i_r \quad \text{Eq. 5.2}$$

It is noted that while the results from Equations 5 and 5.2 are satisfactory, eight equations must be utilized with 6 thresholds using 11 coefficients and 68 current measurements. This adds computational burden to the microcontroller while increasing complexity and a greater likelihood of mistakes being made in the firmware of the microcontroller.

I have therefore discovered a heretofore novel technique that allows the acquisition of glucose result substantially just as accurate as the known technique but much simpler by being based on a logarithm of a ratio of two measured currents. Unexpectedly, it was discovered that this logarithm of the current ratio is strongly and linearly related to the glucose concentration of the physiological fluid sample and weakly related to the hematocrits of the fluid sample. That is, the new but simpler technique is just as accurate as the known (but complex) technique yet the new technique is generally insensitive to the interfering effects of hematocrits.

This new technique involves the use of two current measurements: (1) a first current $I_1$, at a first polarity, obtained at least at any point in the current transient CT over the time range defined by 602 in the current output transient CT during and after the switch in the first voltage E1 to the second voltage E2 (e.g., typically from about 1 seconds to about 4 seconds from the start of the test sequence in FIG. 6B); and (2)

a second current $I_2$, at preferably an opposite polarity to the first current, obtained at least at any point in current transient CT over the entire time range defined by 604 in the current output transient CT after the third voltage E3 is maintained (e.g., typically from about 4 seconds to about 5.5 seconds from the start of the test sequence). An absolute value of a ratio of the first current $I_1$ to the second current $I_2$ is represented by "r". Then the logarithm of such ratio (multiplied with the second current) is represented by a quantity X (with magnitudes in microamperes). Quantity X is strongly and linearly related to the glucose concentration of the physiological fluid sample and weakly related or basically insensitive to the hematocrits of the fluid sample. Glucose concentration or "G" can therefore be determined based on the "intercept" or $I_T$ resulting from linear regression analysis of the current transient of a batch of biosensors and "slope" of $S_L$ of the current transient from the same batch of biosensors.

To summarize, a glucose result can be determined from the following series of measurements and calculations in Equations 6.1-6.3:

$$G = I_T + S_L * X \qquad \text{Eq. 6.1}$$

$$X = \log(kr)I_2 \qquad \text{Eq. 6.2}$$

$$r = \left|\frac{I_1}{I_2}\right| \qquad \text{Eq. 6.3}$$

Where: G is representative of glucose concentration
$I_T$ represents the intercept resulting from linear regression analysis of a batch of biosensors;
$S_L$ represents the slope resulting from linear regression analysis of a batch of biosensors;
$I_1$ represents a first current at a first polarity measured from the current transient at any time point from about 1 seconds to about 4 seconds from a start of the test sequence;
$I_2$ represents a second current at a second polarity measured from the current transient at any time point from about 4 seconds to about 6 seconds from the start of the test sequence;
X represents a current magnitude proportional to the glucose concentration; and
k represents a coefficient from about 1 to about 2.

Equations 6.1-6.3 can be combined together to provide for Equation 6.4:

$$G = I_T + S_L * \log\left(k\left|\frac{I_1}{I_2}\right|\right)I_2 \qquad \text{Eq. 6.4}$$

From Equation 6.1, it is clear that the glucose concentration G is generally the logarithm of the ratio of the first current to the second current and that the other terms $I_T$, $S_L$ and k are specific to the manufacturing parameters of a particular batch of strips.

Instead of a current measured at a specific time point for $I_1$ or $I_2$, a summation of currents measured during a predetermined interval for each of the first current and second current in which the time interval is referenced with respect to the start time of the test sequence. In one example, the first current can be a summation of measured current outputs at about 1.4 seconds from the start time to about 4 seconds from the start time, and the second current can be a summation of the measured current outputs at about 4.2 seconds from the start time to about 5 seconds from the start time. The current outputs can be sampled for summation at a suitable interval such as for example, every 5 milliseconds to 50 milliseconds. The first and second current outputs can be in the respective forms:

$$I_1 = \sum_{t=1.4secs}^{t=4secs} i(t) \qquad \text{Eq. 6.5}$$

$$I_2 = \sum_{t=4.2secs}^{t=5secs} i(t) \qquad \text{Eq. 6.6}$$

In summary, it can be seen that an analyte concentration can be determined with three equations, two current measurements and one coefficient in contrast to the known technique, which utilizes eight equations with 6 thresholds using 11 coefficients and 68 current measurements. Moreover, my new technique is simpler and allows for faster computation of the analyte concentration, verification testing demonstrated that the new technique (FIG. 7B) is comparable to the known technique (FIG. 7A) within the ISO requirement of ±15 mg/dL or 15% of referential analyte datum, whichever is larger. Not only is the new technique simpler, it is generally unaffected by the interfering effects of hematocrit across the range of 20% to 60% hematocrits.

Figure 7A:
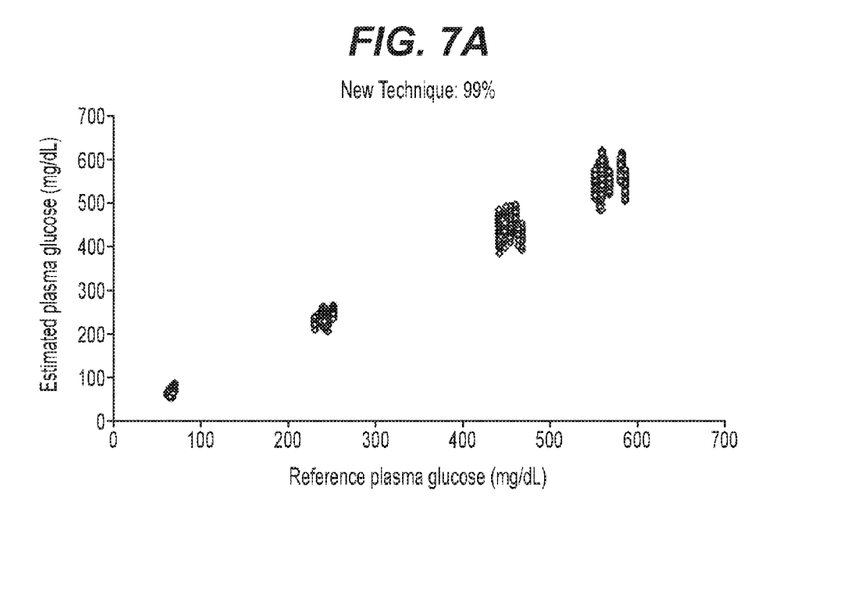
FIG. 7A illustrates the accuracy of the new and simpler technique for approximately two thousand test samples as compared to actual values of the samples.

As shown in FIG. 7A for the new technique, approximately 2160 test strips were measured with glucose concentrations ranging from about 61 mg/dL to about 585 mg/dL (hematocrits from 19%-61%) for three different batches of strips. With the first current output $I_1$ measured at about 2.25 seconds from the start of test sequence, the second current output $I_2$ measured at about 4.4 seconds from the start of the test sequence and coefficient k of about 2.5, results from FIG. 7A show that about 99.0% of the glucose concentrations are within the ISO requirements for calculations based on the new technique (i.e., "calculated glucose results" on the y-axis of FIG. 7A) with respect to laboratory grade measurement (i.e., "actual glucose results" on the x-axis of FIG. 7A). The new technique resulted in about 99.0% of the test samples being within the ISO requirements, compares very well with the more complex and computationally intensive but known technique, which resulted in about 99.8% of the test samples being within the ISO requirements, shown here in FIG. 7B.

Figure 7B:
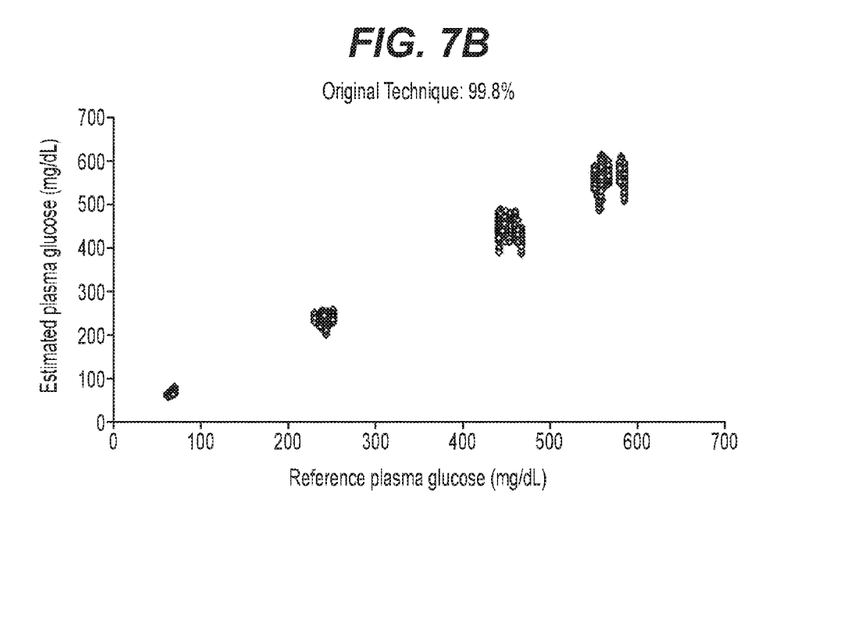
FIG. 7B illustrates the accuracy of the known but computationally complex technique for approximately two thousand test samples as compared to actual values of the samples.
Figure 8:
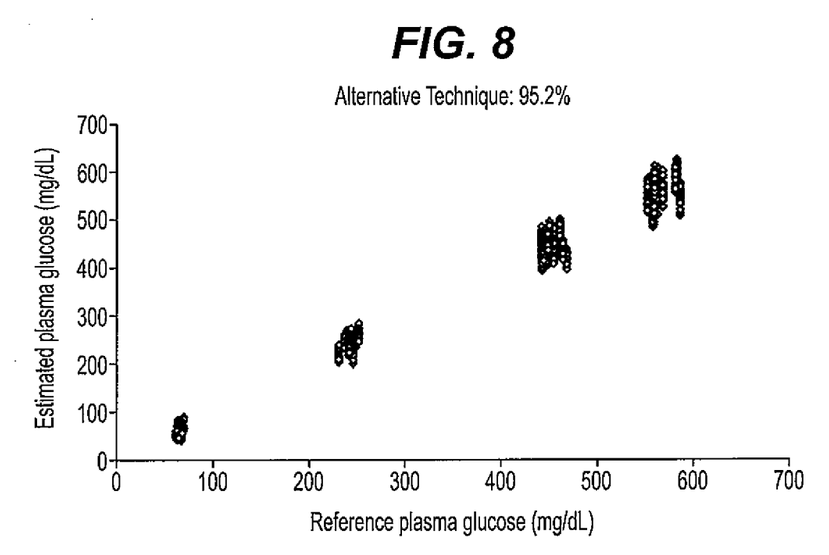
FIG. 8 illustrates the accuracy of an alternative technique for approximately two-thousand samples that compares well with the known technique in FIG. 7B.

One skilled in the art would understand that selection of different time points for the first and second current will provide different results such that some results may be more accurate or less accurate than the original technique of FIG. 7B. For example, in an alternate embodiment, where the first current output $I_1$ is measured at about 4 seconds and the second current output $I_2$ is measured at about 5 seconds with coefficient k being set to about 1.2, the results in FIG. 8 indicate that about 95.2% of the measured samples were within the ISO requirements as compared to the results in FIG. 7A (99%) or in FIG. 7B (99.8%).

While the alternate embodiment may not have as high a percentage of the glucose concentrations being within ISO requirements, it is believed that this value is still viable in its intended use as analyte test strips.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method of determining blood glucose concentration with a glucose measurement system that includes a test strip and test meter, the test meter having a microcontroller configured to apply a plurality of test voltages to the test strip and measure a current transient output resulting from an electrochemical reaction in a test chamber of the test strip, the method comprising:
   initiating a test sequence after deposition of a sample;
   transforming glucose in the sample from one form to a different form;
   switching a first voltage to a second voltage different than the first voltage;
   changing the second voltage to a third voltage different from the second voltage;
   measuring a first current output of a current transient from the electrodes at least at any point during and after the switching from the first voltage to the second voltage;
   measuring a second current output of the current transient at least at any point during and after the third voltage is maintained in the test chamber; and
   calculating a blood glucose concentration based on a logarithm of a ratio of the first and second current outputs.

2. The method of claim 1, in which the calculating comprises utilizing an equation of the form:

$$G = I_T + S_L * \log\left(k\left|\frac{I_1}{I_2}\right|\right)I_2$$

where G is representative of glucose concentration
   $I_T$ comprises a magnitude of an intercept resulting from linear regression analysis of a batch of test strips;
   $S_L$ comprises a magnitude of a slope resulting from linear regression analysis of a batch of test strips;
   $I_1$ comprises a first current output measured from the current transient at any time point from about 1 seconds to about 4 seconds from a start of the test sequence;
   $I_2$ comprises a second current output measured from the current transient at any time point from about 4 seconds to about 5 seconds from the start of the test sequence; and
   k comprises a coefficient from about 1 to about 4.

3. The method of one claim 1 or claim 2, in which the first current output is measured at about 2.25 seconds after the start of a test sequence and the second current output is measured at about 4.4 seconds after the start of the test sequence and k comprises about 2.5.

4. The method of one claim 1 or claim 2, in which the first current output comprises a summation of current outputs measured from about 1 seconds after the start of the test sequence to about 4 seconds after the start of the test sequence and the second current output comprises a summation of current outputs measured from about 4.2 seconds after the start of the test sequence to about 5 seconds after the start of the test sequence.

5. The method of one of claim 1 or claim 2, in which the first current output is measured at about 4 seconds after the start of a test sequence and the second current output is measured at about 5 seconds after the start of the test sequence and k comprises about 1.2.

6. The method of claim 1, in which the step of switching comprises changing the polarity of the second voltage with respect to the first voltage.

7. An analyte measurement system comprising:
   a biosensor having at least two electrodes with reagent disposed proximate the electrodes; and
   an analyte meter including a port for insertion of the biosensor for electrical connection with a microcontroller of the meter and the at least two electrodes such that, upon deposition of an fluid sample, a test sequence is initiated by the microcontroller to measure first and second current outputs from voltages applied to the electrodes of the biosensor and determine an analyte concentration based on a logarithm of the ratio of the first and second currents.

8. The system of claim 7, in which the microcontroller is configured to calculate a glucose concentration from an equation of the form:

$$G = I_T + S_L * \log\left(k\left|\frac{I_1}{I_2}\right|\right)I_2$$

where G is representative of glucose concentration
   $I_T$ comprises a magnitude of an intercept resulting from linear regression analysis of a batch of biosensors;
   $S_L$ comprises a magnitude of a slope resulting from linear regression analysis of a batch of biosensors;
   $I_1$ comprises a first current output measured from a current transient at any time point from about 1 seconds to about 4 seconds from a start of the test sequence;
   $I_2$ comprises a second current output measured from the current transient at any time point from about 4 seconds to about 5 seconds from the start of the test sequence; and
   k comprises a coefficient from about 1 to about 4.

9. The system of claim 8, in which the first current output is measured at about 2.25 seconds after the start of a test sequence and the second current output is measured at about 4.4 seconds after the start of the test sequence and k comprises about 2.5.

* * * * *